United States Patent
Reisberg

(10) Patent No.: US 8,900,281 B2
(45) Date of Patent: Dec. 2, 2014

(54) DEVICE FOR OSTEOSYNTHESIS AND FOR IMMOBILIZATION AND STABILISATION OF TUBULAR BONES

(76) Inventor: Erhard Reisberg, Eschbach (DE)

( * ) Notice: Subject to any disclaimer, the term of this patent is extended or adjusted under 35 U.S.C. 154(b) by 392 days.

(21) Appl. No.: 12/997,590

(22) PCT Filed: May 27, 2009

(86) PCT No.: PCT/EP2009/056425
§ 371 (c)(1),
(2), (4) Date: Jan. 1, 2011

(87) PCT Pub. No.: WO2009/150047
PCT Pub. Date: Dec. 17, 2009

(65) Prior Publication Data
US 2011/0106182 A1 May 5, 2011

(30) Foreign Application Priority Data

Jun. 12, 2008 (DE) .......................... 10 2008 002 389

(51) Int. Cl.
| | |
|---|---|
| A61B 17/04 | (2006.01) |
| A61B 17/84 | (2006.01) |
| A61F 2/08 | (2006.01) |
| A61B 17/80 | (2006.01) |
| A61B 17/82 | (2006.01) |

(52) U.S. Cl.
CPC ............ *A61B 17/8076* (2013.01); *A61B 17/82* (2013.01)
USPC .............. 606/324; 606/283; 606/284; 606/75

(58) Field of Classification Search
USPC .................................. 606/75, 283–284, 324
See application file for complete search history.

(56) References Cited

U.S. PATENT DOCUMENTS

| | | | |
|---|---|---|---|
| 4,263,904 A | 4/1981 | Judet | |
| 4,364,382 A | 12/1982 | Mennen | |

(Continued)

FOREIGN PATENT DOCUMENTS

| | | |
|---|---|---|
| DE | 27 36 972 A1 | 3/1979 |
| DE | 82 19 491.2 U1 | 11/1983 |

(Continued)

OTHER PUBLICATIONS

Office Action issued by the Japan Patent Office on Jul. 23, 2013, regarding the above-referenced application's counterpart application in Japan (Appl. No. 2011-512924).

*Primary Examiner* — Andrew Yang
*Assistant Examiner* — Olivia C Chang
(74) *Attorney, Agent, or Firm* — Pai Patent & Trademark Law Firm; Chao-Chang David Pai

(57) ABSTRACT

FIG. 1 shows an inventive implant 1. It has a central fillet 2 extending along a longitudinal axis L. The fillet 2 has openings 3 which are formed at regular intervals. At the level of the openings 3 and extending at right angles on both sides are clamps 4, which, when the implant is inserted, are brought into mutual engagement with a tubular bone and clamped to it. The fillet 2 is formed so as to be bendable in three-dimensions. It can be bent in two planes relative to the longitudinal axis L of the fillet 2 and torqued about the longitudinal axis L. Thus, a simple implant 1 with an overall regular structure is provided which can be cut with a cutting pliers to a desired length.

20 Claims, 2 Drawing Sheets

(56) References Cited

U.S. PATENT DOCUMENTS

| | | | |
|---|---|---|---|
| 2003/0055429 A1* | 3/2003 | Ip et al. ........................... | 606/69 |
| 2006/0085000 A1 | 4/2006 | Mohr et al. | |
| 2008/0082101 A1* | 4/2008 | Reisberg ......................... | 606/60 |

FOREIGN PATENT DOCUMENTS

| | | |
|---|---|---|
| DE | 38 08 937.8 A1 | 10/1989 |
| DE | 103 01 692 A1 | 8/2004 |
| DE | 10 2006 042 277 A1 | 3/2008 |
| EP | 0 024 635 A1 | 3/1981 |
| FR | 2353274 A | 12/1977 |
| JP | H03-012145 A | 1/1991 |
| JP | 1992-060211 U | 5/1992 |
| JP | 03012145 A | 12/1999 |
| JP | 2002-501776 A | 1/2002 |
| JP | 2003-102743 A | 4/2003 |
| JP | 2003-210478 A | 7/2013 |

\* cited by examiner

DEVICE FOR OSTEOSYNTHESIS AND FOR IMMOBILIZATION AND STABILISATION OF TUBULAR BONES

FIELD OF THE INVENTION

The invention relates to a device for the osteosynthesis and immobilization and stabilisation of tubular bones, comprising a carrier fillet extending in a first longitudinal direction, at least one first clamp extending laterally from the carrier fillet and a second clamp extending laterally from the carrier fillet, said second clamp being longitudinally offset from the first clamp.

PRIOR ART

After fractures or osteotomies of tubular bones, such as in the thorax region, the thorax needs to be stabilised to permit the bones to knit together. Stabilisation is mostly carried out conservatively, i.e. not invasively, from the outside. Nonetheless, the burden on the patient is significant. For example, the patient's breathing and mobility may be restricted. An improvement in his condition occurs only after a relatively long period of convalescence.

Where treatment involves surgical intervention, it is standard practice to immobilize the bones with surgical wire or osteosynthesis wire or other materials. These methods, however, suffer in particular from the disadvantage that the desired exercise stability, i.e. a state in which the thorax can undergo slight loading, is usually not achieved immediately.

To counter this, publication DE 10 2006 042 277 A1 proposes an implant for osteosynthesis that consists essentially of two rib clamps and a connecting rod. The connection between two bone ends is effected by immobilizing a clamp at each bone end, then connecting the clamps to the connecting rod. The connecting rods are provided in a kit in different lengths, along with the clamps. With the help of this system exercise stability which is needed is obtained immediately during surgery for fractures or osteotomies.

OBJECT OF THE INVENTION

Proceeding from the known prior art, the object of the present invention is to provide a device for osteosynthesis, which is simple to use and is versatile.

TECHNICAL SOLUTION

This object is achieved by a device for osteosynthesis and for immobilizing and stabilising tubular bones according to claim 1. Advantageous embodiments are the subject of the dependent claims.

The inventive device for the osteosynthesis as well as the immobilization and stabilisation of tubular bones comprises a carrier fillet extending in a first longitudinal direction, at least a first clamp extending laterally from the carrier fillet and a second clamp extending laterally from the carrier fillet, said second clamp being longitudinally offset from the first clamp. The fillet has at least one area arranged between the first clamp and second clamp that is formed so as to be bendable relative to the longitudinal axis of the fillet.

The device is thus formed as an implant or rib clamp that consists essentially of at least two clamps which extend from both sides of a fillet and for the purpose of being attached to either end of a tubular bone. The first clamp is required for attachment to one side of the fracture/osteotomy, the second clamp for attaching the implant to the second side of the fracture/osteotomy. The fracture is bridged by the longitudinal fillet.

The implant can theoretically have two clamp pairs, but is preferably formed with a plurality of clamp pairs. Especially for oblique fractures/osteotomies, it may be advantageous to use two or three clamp pairs per side for the purpose of attaching the implant.

The device can be produced relatively easily and be provided with great fillet length or a plurality of clamp pairs that extend from the fillet. The implant may theoretically be provided as an "endless clamp" such that it can be cut to size by the surgeon.

In accordance with the invention, the fillet is bendable between the at least two clamps. If a fillet is provided with several clamps, it is preferably formed so as to be bendable between all clamps relative to the longitudinal axis. In this way, the shape of the implant can be adjusted to virtually any type of bone surface or contour.

The first clamp and the second clamp, too, are formed so as to be capable of bending in order that, after mutual engagement with the tubular bone, they may be immobilized on it.

The implant can be universally attached to round or oval-shaped tubular bones, such as rib bones. For this, the clamp is immobilized on both sides of the fracture. The bone segments are brought together beforehand into an optimal position and stabilised by means of the inventive implant. The biological process of osteo-synthesis is thus assisted. The implant can either be removed after reossification or be left in the body.

The device can thus be provided as a kit comprising just a few parts and versatile applications. Handling is easy for the surgeon, as only a one-piece implant is required for connecting two tubular bone ends.

In particular, the fillet is formed so as to be bendable in at least two dimensions relative to the longitudinal axis. For example, the fillet can be bent in any two non-parallel planes that intersect in the longitudinal axis.

Preferably, the fillet can have at least one area arranged between the first clamp and second clamp that permits the first clamp to be twisted about the longitudinal axis of the fillet relative to the second clamp. In other words, the fillet can be bent or torqued, so that the 3D osteosynthesis device can be three-dimensionally adjusted to any contour or bone structure. The adjustment is effected, for example, by means of flat-nose pliers for bending the fillet up or down or for applying torque. By means of a three-point pliers, the fillet can be bent laterally, that is, parallel with the front of the fillet, relative to the longitudinal axis. The three-point pliers, for example, permits bending through an angle of about 15° towards each side and between each pair of clamps.

For immobilizing the first clamp and the second clamp, following the mutual engagement with the tubular bone, a clamp-immobilizing pliers may be used which can be inserted, for example perpendicularly to the clamp. However, an angled pliers can also be used that permits access to the implant through a prepared soft tissue tunnel.

Furthermore, a fillet-cutting pliers for cutting off a suitable length of implant and a three-point pliers may possibly be used to bend the fillet in a suitable manner.

In a preferred embodiment of the invention, at least the first clamp and/or the second clamp extend from both sides of the fillet. Each clamp thus has two prongs that can be adapted around a tubular bone.

Especially, the first clamp and/or the second clamp are each formed as a circular segment with an engagement opening for mutual engagement with a tubular bone. For the purpose of attachment, the bone must be at least partially enclosed by the clamp from the rear. Therefore, different sized clamps can be provided for different applications and bone diameters. The clamps are provided with a defined width, i.e. a defined distance between the preferably semi-circularly pre-bent lateral pairs of clamps. The engagement opening can be widened or narrowed, for example, by means of a flat-nose pliers, before the implant is inserted.

It is also possible to provide the device in variants of different size for different bones.

Preferably, the fillet is configured as a strip of material of predetermined length and width. The width of the fillet can be constant along the longitudinal axis, but in particular may also vary. Thus, the fillet, especially in that area between the clamps in which the bar is bendable, can be provided in a reduced width to facilitate bending, such as lateral bending. The fillet width, depending on the application, can be about 2 to 6 mm for a material thickness, for example, of 1 to 4 mm.

In a particularly preferred embodiment of the invention, the fillet has at least two openings which are arranged along the longitudinal axis of the fillet. The openings or drill holes can be formed at regular intervals along the central fillet.

In particular, the fillet has openings for engaging a tool for bending and/or torquing the bendable area of the fillet. The openings can be formed so as to engage a three-point pliers for lateral bending of the fillet.

Especially, the openings are each arranged along the longitudinal axis of the fillet at the level of a clamp.

In a preferred embodiment, the openings are arranged between the bendably formed areas of the fillet. As part of the invention, the openings are formed and arranged such that, upon engagement of a tool, such as a three-point pliers, proper bending of a bendable area causes, where possible, no deformation of the opening, but rather only deformation of the bendable areas of the fillet.

Especially, one opening is provided at the level of every clamp on the device.

Preferably, the fillet and the clamps extending from the fillet are formed in one piece. This greatly facilitates the provision and handling of the implant since, on one hand, it allows a standard clamp for all kinds of fracture to be provided and to be shortened by the surgeon to the desired length and, on the other hand, the surgeon does not have to join individual parts together during the operation.

Preferably, the device is made of an implantable material, especially titanium. However, the device can be made from all sorts materials suitable for implantation into the human body, such as suitable metals, resorbable materials, memory materials, etc.

Pure titanium is particularly suitable on account of its biocompatibility and bio-inertness. Titanium thus also makes a suitable long-term implant, whereas conventional implant steel loses its body compatibility over time. Since the oxide layer of titanium renews itself spontaneously even after bending in biological milieu, titanium implants remain chemically inert and corrosion resistant for a long time as well. With regard to the present invention, titanium implants can be deformed relatively precisely and can therefore be adapted exactly to the individual bone contours of the patient.

Preferably, the device has a plurality of clamps and/or a plurality of openings, with the structure of the device being repeated at regular intervals along the longitudinal axis. Two or more clamps are needed that are arranged longitudinally offset on the fillet. Preferably, the device has more than two clamps which are arranged at regular intervals along the longitudinal axis of the fillet. At the level of each clamp, an opening may be arranged for engagement of a bending tool.

In a particularly preferred embodiment of the invention, the device is composed of structural elements, each comprising a clamp and a fillet area, the structure being repeated n times, where n=1, 2, 3, . . . . Thus, a simple implant with an overall regular structure is provided which can be cut with a cutting pliers to a desired length, once this has been determined.

BRIEF DESCRIPTION OF THE FIGURES

Other features and advantages of the invention are apparent from the description of a preferred embodiment according to the attached drawings. The drawings show in
FIG. 1 a perspective view of an inventive implant.

DESCRIPTION OF A PREFERRED EMBODIMENT

Figure 1:
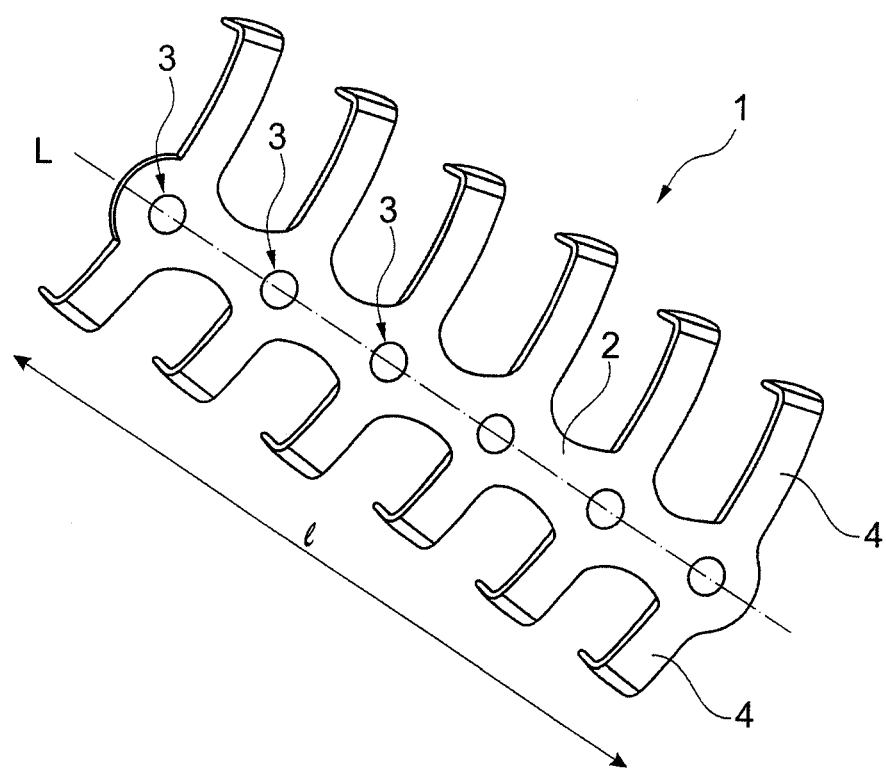

FIG. 1 shows an inventive implant 1. It has a central fillet 2 extending along a longitudinal axis L. The fillet 2 has a length 1, in which openings 3 are formed at regular intervals. At the level of the openings 3 and extending at right angles on both sides are clamps (pairs of clamps) 4, which, when the implant 1 is inserted, are brought into mutual engagement with a tubular bone and clamped to it.

Figure 2:
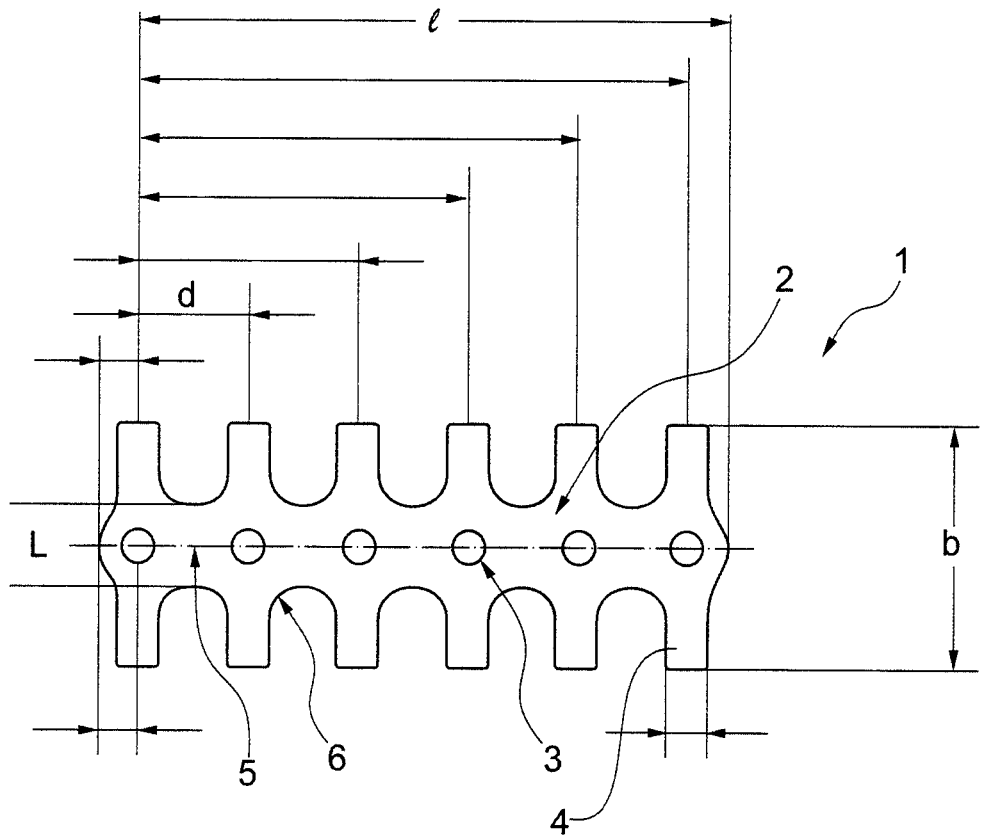
FIG. 2 a plan view of the inventive implant.

FIG. 2 is a schematic diagram of implant 1 in a plan view. Openings 3 and clamps 4 are formed or arranged at regular intervals d on fillet 2. The width b of the implant 1 is defined by the distance between the clamps 4 extending semicircularly into the plane of the figure.

The fillet 2 is formed as a thin strip of material in which the openings 3 are formed for engaging a bending tool, particularly a three-point pliers. Bending occurs on one hand in the drawing plane relative to the longitudinal axis L, especially in the areas 5 between the openings 3. In these areas 5, the fillet has radial contours 6, such that—in the picture plane—constrictions are created for facilitating bending and twisting in the areas 5.

In addition to bending in the drawing plane, the areas 5 of fillet 2 can be bent perpendicularly or obliquely to the drawing plane relative to the longitudinal axis L. This bending, for example, can be carried out with a pair of flat-nose pliers. In addition, the fillet can 2 can be twisted (torqued) by applying a torque about the longitudinal axis L. Thus, two adjacent clamps 4 are twisted relative to each other. Overall, in this way it is possible to three-dimensionally adjust the implant 1 to a given bone structure.

Figure 3:
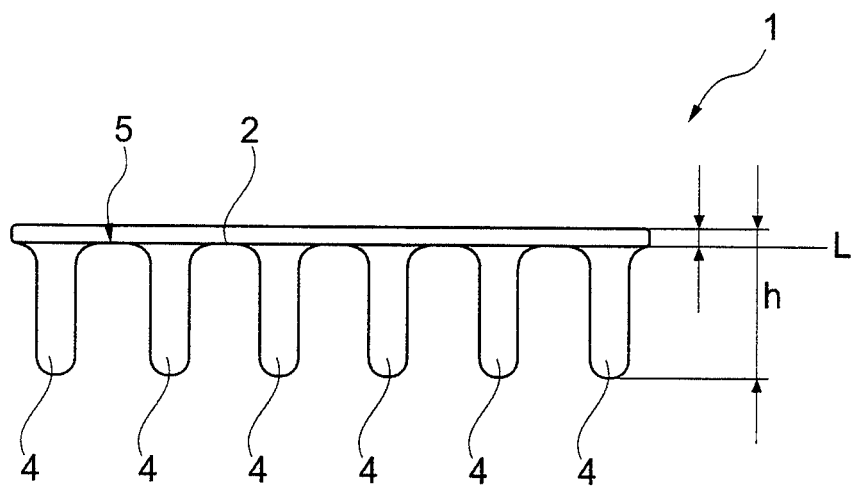
FIG. 3 a side view of the inventive implant.

FIG. 3 shows the implant 1 in side view. From the fillet 2 formed as a thin strip, the clamps 4 extend laterally downwards. The height h of the implant 1 is determined by the distance from the top side of the fillet 2 to the lower ends of the clamps 4. The fillet 2, especially in the areas 5, can be adjusted to a bone structure in three dimensions, in the drawing plane relative to the longitudinal axis L, perpendicularly to the drawing plane relative to the longitudinal axis L, and by twisting the fillet 2 about the longitudinal axis L.

The invention claimed is:

1. A device (1) for the osteosynthesis as well as the immobilization and stabilisation of tubular bones, comprising a carrier fillet (2) extending in a longitudinal direction along a longitudinal axis (L), a first clamp (4) having two prongs respectively extending laterally from two sides of the carrier fillet (2) and a second clamp (4) having two prongs respectively extending laterally from two sides of the carrier fillet (2), said second clamp (4) being longitudinally offset from the first clamp (4), characterised by the fact that
the fillet (2) has at least one area (5) arranged between the first clamp (4) and second clamp (4) that is formed so as to be bendable relative to the longitudinal axis of the fillet (2) such that the device is three-dimensionally adjustable to any contour or bone structure;
the two prongs of each of the first clamp and the second clamp are adaptable to clamp around a tubular bone for engaging the device (1) with the tubular bone without bone screws or other fixing means; and
the fillet (2) has at least two openings (3) that are arranged along the longitudinal axis (L) of the fillet (2), each of the openings being provided for engagement of a pair of three-point pliers for bending or torquing the at least one bendable area (5), wherein
each of the openings (3) is arranged at the level of one of the clamps (4).

2. The device (1) in accordance with claim 1, characterised by the fact that
the fillet (2) is formed so as to be bendable in at least two dimensions relative to the longitudinal axis (L).

3. The device (1) in accordance with claim 1, characterised by the fact that
the fillet (2) has at least one area (5) arranged between the first clamp (4) and second clamp (4) that permits the first clamp (4) to be twisted about the longitudinal axis (L) of the fillet (2) relative to the second clamp (4).

4. The device (1) in accordance with claim 1, characterised by the fact that
the two prongs of at least one of the first clamp (4) and the second clamp (4) form a circular segment with an engagement opening for mutual engagement with a tubular bone.

5. The device (1) in accordance with claim 1, characterised by the fact that
the openings (3) are arranged adjacent the at least one bendable area (5) of the fillet (2).

6. A device (1) for the osteosynthesis as well as the immobilization and stabilisation of tubular bones, comprising a carrier fillet (2) extending in a longitudinal direction along a longitudinal axis (L), a first clamp (4) having two prongs respectively extending laterally from two sides of the carrier fillet (2) and a second clamp (4) having two prongs respectively extending laterally from two sides of the carrier fillet (2), said second clamp (4) being longitudinally offset from the first clamp (4), wherein
the fillet (2) has at least one area (5) arranged between the first clamp (4) and second clamp (4) that is formed so as to be bendable relative to the longitudinal axis of the fillet (2) such that the device is three-dimensionally adjustable to any contour or bone structure;
the two prongs of each of the first clamp and the second clamp are adaptable to clamp around a tubular bone for engaging the device (1) with the tubular bone without bone screws or other fixing means; and
the fillet (2) has at least two openings (3) that are arranged along the longitudinal axis (L) of the fillet (2), each of the openings being provided for engagement of a pair of three-point pliers for bending or torquing the at least one bendable area (5), wherein
a respective opening (3) is provided at the level of each clamp (4) of the device (1).

7. The device (1) in accordance with claim 1, characterised by the fact that
the fillet (2) and the clamps (4) extending from the fillet (2) are formed in one piece.

8. The device (1) in accordance with claim 1, characterised by the fact that
the device (1) is produced from an implantable material.

9. The device (1) in accordance with claim 1, characterised by the fact that
the device (1) has a plurality of clamps (4) and a plurality of openings (3), with the structure of the device (1) repeated at regular intervals along the longitudinal axis (L) of the fillet (2).

10. The device (1) in accordance with claim 1, characterised by the fact that
the device (1) is composed of structural elements, each comprising a clamp (4) and a fillet area, and the structure repeats itself n times along the longitudinal axis of the fillet (2), where n is an integer greater than or equal 2.

11. The device (1) in accordance with claim 8, characterised by the fact that
the implantable material is titanium.

12. The device (1) in accordance with claim 6, characterised by the fact that
the fillet (2) is formed so as to be bendable in at least two dimensions relative to the longitudinal axis (L).

13. The device (1) in accordance with claim 6, characterised by the fact that
the fillet (2) has at least one area (5) arranged between the first clamp (4) and second clamp (4) that permits the first clamp (4) to be twisted about the longitudinal axis (L) of the fillet (2) relative to the second clamp (4).

14. The device (1) in accordance with claim 6, characterised by the fact that
the two prongs of at least one of the first clamp (4) and the second clamp (4) form a circular segment with an engagement opening for mutual engagement with a tubular bone.

15. The device (1) in accordance with claim 6, characterised by the fact that
the openings (3) are arranged adjacent the at least one bendable area (5) of the fillet (2).

16. The device (1) in accordance with claim 6, characterised by the fact that
the fillet (2) and the clamps (4) extending from the fillet (2) are formed in one piece.

17. The device (1) in accordance with claim 6, characterised by the fact that
the device (1) is produced from an implantable material.

18. The device (1) in accordance with claim 6, characterised by the fact that
the device (1) has a plurality of clamps (4) and a plurality of openings (3), with the structure of the device (1) repeated at regular intervals along the longitudinal axis (L) of the fillet (2).

19. The device (1) in accordance with claim 6, characterised by the fact that
the device (1) is composed of structural elements, each comprising a clamp (4) and a fillet area, and the structure repeats itself n times along the longitudinal axis of the fillet (2), where n is an integer greater than or equal 2.

20. The device (1) in accordance with claim 17, characterised by the fact that
the implantable material is titanium.

* * * * *